United States Patent [19]

Hofer et al.

[11] 4,112,080
[45] Sep. 5, 1978

[54] O-ALKYL-S-[1,6-DIHYDRO-6-OXO-PYRIDAZIN(1)YLMETHYL]-(THIONO)-(DI)-THIOLPHOSPHORIC(PHOSPHONIC) ACID ESTERS

[75] Inventors: Wolfgang Hofer; Fritz Maurer; Hans-Jochem Riebel; Lothar Rohe, all of Wuppertal; Ingeborg Hammen, Cologne; Bernhard Homeyer, Opladen, all of Germany

[73] Assignee: Bayer Aktiengesellschaft, Leverkusen, Germany

[21] Appl. No.: 645,984

[22] Filed: Jan. 2, 1976

Related U.S. Application Data

[63] Continuation of Ser. No. 451,321, Mar. 13, 1974, abandoned.

[30] Foreign Application Priority Data

Mar. 13, 1974 [DE] Fed. Rep. of Germany ....... 2316821

[51] Int. Cl.² .......................... A01N 9/36; C07F 9/65
[52] U.S. Cl. .................................. 424/200; 544/232; 544/241; 544/240; 544/237
[58] Field of Search ................ 424/200; 260/250 AP, 260/250 P

[56] References Cited

U.S. PATENT DOCUMENTS 2,938,902  3/1960  De Breuil ........................... 260/250

FOREIGN PATENT DOCUMENTS 2,006,020  9/1971  Fed. Rep. of Germany ...... 260/25 AP
970,905  9/1964  United Kingdom ................ 260/250 P Primary Examiner—Donald G. Daus
Assistant Examiner—Mark L. Berch
Attorney, Agent, or Firm—Burgess, Dinklage & Sprung

[57] ABSTRACT

O-Alkyl-S-[1,6-dihydro-6-oxo-pyridazin(1)ylmethyl]-(thiono)-(di)-thiolphosphoric(phosphonic) acid esters of the formula

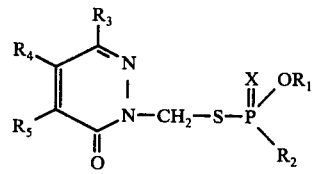

in which $R_1$ is alkyl or alkoxyalkyl with 1 to 6 carbon atoms per alkyl chain, $R_2$ is alkyl, alkylmercapto, alkylamino or alkenylamino with up to 6 carbon atoms per aliphatic chain, amino or phenyl, and $R_3$ is alkoxy, cyanoalkoxy, carbalkoxy-alkoxy, alkenyloxy, alkynyloxy, alkanoyloxy, dialkylcarbamoyloxy or alkylsulfonyloxy with up to 5 carbon atoms in each aliphatic chain, halogen, hydroxyl, or a (thiono) (thiol)-phosphoric(phosphonic) acid ester or esteramide radical, $R_4$ and $R_5$ each independently is hydrogen, alkyl with 1 to 3 carbon atoms or halogen, or $R_4$ and $R_5$ conjointly form a fused benzene ring, and X is oxygen or sulfur, which possess insecticidal, acaricidal and nematocidal properties.

10 Claims, No Drawings

O-ALKYL-S-[1,6-DIHYDRO-6-OXO-PYRIDAZIN(-1)YLMETHYL]-(THIONO)-(DI)-THIOLPHOS-PHORIC(PHOSPHONIC) ACID ESTERS

This is a continuation, Ser. No. 451,321, filed Mar. 13, 1974, now abandoned.

The present invention relates to and has for its objects the provision of particular new O-alkyl-S-[1,6-dihydro-6-oxo-pyridazin(1)ylmethyl]-(thiono)-(di)-thiolphosphoric (phosphonic) acid esters, i.e. O,O-dialkyl-S-[1,6-dihydro-6-oxo-pyridazin(1)ylmethyl]-thiolphosphoric acid esters, the O-alkyl-N-alkyl- or -alkenyl ester amide counterparts, the alkanephosphonic acid ester and ester-amide counterparts, the O,S-dialkyl ester counterparts, the corresponding O-alkoxyalkyl-esters and ester-amides, their thiono counterparts, and variously substituted derivatives thereof, which possess insecticidal, acaricidal and nematocidal properties, active compositions in the form of mixtures of such compounds with solid and liquid dispersible carrier vehicles, and methods for producing such compounds and for using such compounds in a new way espcially for combating parts, e.g. insects, acarids and nematodes, with other and further objects becoming apparent from a study of the within specification and accompanying examples.

It has been disclosed in French Patent Specification 1,231,293 that certain S-[1,6-dihydro-6-oxo-pyridazin(-1)ylmethyl]-(thiono)-thiol-phosphoric acid esters, for example O,O-diethyl-S-[1,6-dihydro-6-oxo-3-chloro- (Compound A) or -3-methoxy- (Compound B) or -3-diethoxythionophosphoryl- oxo-pyridazin(1)ylmethyl]- (Compound C), O,O-di-isopropyl-S-[1,6-dihydro-6-oxo-3-chloro-pyridazin(1)ylmethyl]- (Compound D) and O,O-diethyl-S-[1,2-dihydro-1-oxo-4-chloro-phthalazin(2)-ylmethyl]-thiono-thiolphosphoric acid esters (Compound E), display insecticidal, acarcidical and nematocidal properties.

The present invention provides, as new compounds, the S-[1,6-dihydro-6-oxo-pyridazin(1)ylmethyl]-(thiono)-(di)-thiol-phosphoric(phosphonic) acid ester and ester-amides of the formula

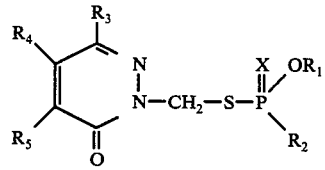

in which
R₁ is alkyl or alkoxyalkyl with 1 to 6 carbon atoms per alkyl chain,
R₂ is alkyl, alkylmercapto, alkylamino or alkenylamino with up to 6 carbon atoms per aliphatic chain, amino or phenyl, and
R₃ is alkoxy, cyanoalkoxy, carbalkoxy-alkoxy, alkenyloxy, alkynyloxy, alkanoyloxy, dialkylcarbamoyloxy or alkylsulfonyloxy with up to 5 carbon atoms in each aliphatic chain, halogen, hydroxyl, or a (thiono) (thiol)-phosphoric(phosphonic) acid ester or ester-amide radical,
R₄ and R₅ each independently is hydrogen, alkyl with 1 to 3 carbon atoms or halogen, or
R₄ and R₅ conjointly form a fused benzene ring, and X is oxygen or sulfur.

Surprisingly, the S-[1,6-dihydro-6-oxo-pyridazin-(1)-ylmethyl]-(thiono)-(di)-thiol-phosphoric(phosphonic) acid ester and ester-amide derivatives according to the invention possess a substantially better insecticidal, including soil-insecticidal, acaricidal and nematicidal action than do previously known compounds of analogous structure and of the same type of action. The compounds according to the invention thus represent a genuine enrichment of the art.

The compounds furthermore contribute to meeting the constant demand for new active compounds in the field of pesticides. This demand arises from the fact that the commercially available agents must, especially in respect to the protection of the environment, meet constantly rising standards, such as low toxicity to warm-blooded animals, low phytotoxicity, rapid degradation in and on the plant with short minimum intervals to be observed between spraying with pesticide and harvesting, and activity against resistant pests.

Preferably R₁ is straight-chain or branched lower alkyl or lower alkoxy-lower alkyl with 1 to 4 carbon atoms per alkyl chain, R₂ is straight-chain or branched lower alkyl, alkylmercapto, alkylamino or alkenylamino with up to 4 carbon atoms per aliphatic chain, amino or phenyl, R₃ is dialkoxy(thiono)-phosphoryloxy, alkanoyloxy, dialkylcarbamoyloxy, alkylsulfonyloxy, alkoxy, alkenyloxy, alkynyloxy or carbalkoxyalkyloxy each with up to 3 carbon atoms per aliphatic chain, chlorine, bromine, hydroxyl or cyanomethyloxy, and R₄ and R₅ are each hydrogen, methyl, ehtyl, chlorine or bromine, or conjointly denote a benzene ring.

The present invention also provides a process for the preparation of an S-[1,6-dihydro-6-oxo-pyridazin(1)ylmethyl]-(thiono)-(di)-thiol-phosphoric(phosphonic) acid ester or ester-amide derivative of the formula (I), in which either (a) a 1,6-dihydro-1-halogenomethyl-6-oxo-pyridazine of the general formula

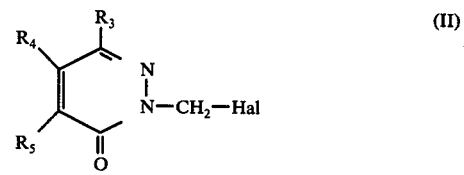

is reacted with a salt of a (thiono)(di)thiol-phosphoric (phosphonic) acid ester or ester-amide, of the general formula

or (b) a phosphorylated 1,6-dihydro-3-hydroxy-6-oxo-pyridazine derivative of the general formula

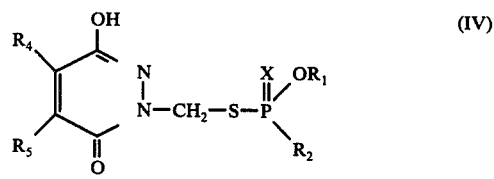

is reached, optionally in the presence of an acid-binding agent, with a halide of the general formula

in which formulas (II) to (V)

R₁ to R₅ and X have the above-mentioned meanings,
Hal is halogen,
Hal₁ is chlorine, bromine or iodine,
M is an alkali metal, alkaline earth metal or ammonium equivalent, and
R₆ is alkyl, carbalkoxy-alkyl, cyanoalkyl, alkenyl, alkynyl, alkanoyl, dialkylcarbamoyl or alkylsulfonyl with up to 5 carbon atoms per aliphatic chain, or a (thiono) (thiol)-phosphoryl(phosphonyl) ester or ester-amide radical.

Preferably Hal is chlorine; R₆ is alkyl, alkenyl, alkynyl, alkylsulfonyl, alkanoyl, dialkylcarbamoyl, dialkoxy(thiono)-phosphoryl or carbalkoxyalkyl with up to 3 carbon atoms per aliphatic chain, or cyanomethyl; and M is sodium or potassium.

If, for example, 1,6-dihydro-1-chloromethyl-3-chloro-6-oxo-pyridazine and the potassium salt of O-ethylmethanethionothiol-phosphonic acid ester or O,O-diethyl-S-[1,6-dihydro-3-hydroxy-6-oxo-pyridazin(1)yl-methyl]-thionothiolphosphoric acid ester and methyl iodide are used as starting substances, the two variants of the process can be represented by the following equations:

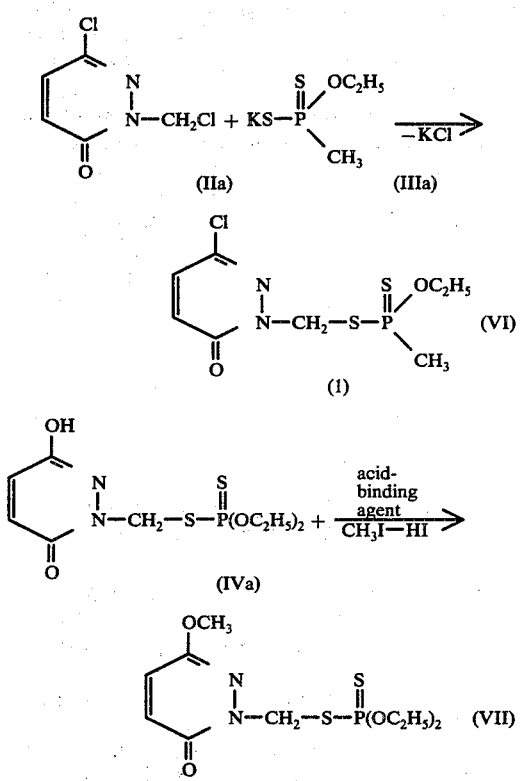

A number of the 1-halogenomethylpyridazinones of the formula (II), to be used as starting materials, have not yet been described in the literature but can be prepared, according to a process which is known in principle, by reacting pyridazin-ones with aqueous formaldehyde solution at elevated temperatures and reacting the hydroxymethyl compounds thereby produced, again at elevated temperature and optionally in a solvent or diluent, with thionyl chloride in accordance with the following equation:

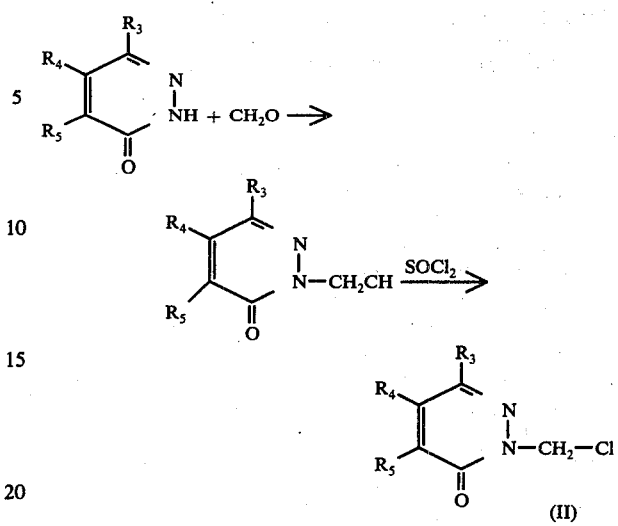

As examples thereof there may be mentioned: 3-chloro-, 3-bromo, 3-hydroxy-, 3-dimethoxyphosphoryloxy-, 3-dimethoxythionophosphoryloxy-, 3-diethoxyphosphoryloxy-, 3-diethoxythionophosphoryloxy-, 3-di-n-propoxyphosphoryloxy-, 3-di-n-propoxythionophosphoryloxy-, 3,4,5-trichloro-, 3-hydroxy-4,5-dichloro-, 3-hydroxy-4,5-dibromo-, 3-chloro-4- or -5-methyl-, 3-chloro-4- or -5-ethyl-1,6-dihydro-6-oxo-1-chloromethylpyridazine, and also 4-chloro-, 4-bromo-, 4-methoxy-, 4-hydroxy-, 4dimethoxyphosphoryloxy-, 4-dimethoxythionophosphoryloxy-, 4-diethoxyphosphoryloxy- and 4-diethoxythionophosphoryloxy-1,2-dihydro-1-oxo-2-chloromethylphthalazine.

The salts of the (thiono)-(di)-thiolphosphoric(phosphonic) acid esters and ester-amides (III), which are also used as starting materials, are in most cases known and can be prepared according to customary methods by treating the corresponding ester halides or ester-amide halides with hydrogen sulfide in the presence of carbonates, or with alcoholic alkali solution, according to the equation:

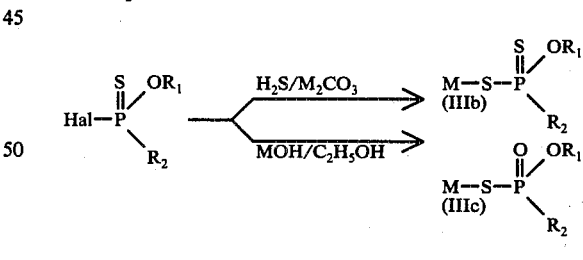

in which
Hal, R₁, R₂ and M have the meanings given above.

As examples thereof, the following may be mentioned: the sodium and potassium salts of O-methyl-, O-ethyl, O-n-propyl-, O-isopropyl-, O-methoxymethyl-, O-ethoxymethyl-, O-ethoxyethyl-, O-ethoxypropyl-methane-, -ethane-, -propane- and -benzene-(thiono)-thiolphosphonic acid esters and also O-methyl-N-methyl-, O-methyl-N-ethyl-, O-methyl-N-n-propyl-, O-methyl-N-isopropyl-, O-ethyl-N-methyl-, O-ethyl-N-ethyl-, O-ethyl-N-n-propyl-, O-ethyl-N-isopropyl-, O-ethyl-N-n-butyl-, O-ethyl-N-allyl-, O-ethyl-N-sec.-butyl-, O-ethyl-N-tert.-butyl, O-methoxymethyl-N-ethyl-, O-ethoxy-ethyl-N-ethyl-, O-n-propoxyethyl-N- n-propyl and O-n-propoxy-ethyl-N-iso-propyl-(thiono)-thiolphosphoric acid ester amides as well as the corresponding unsubstituted amides.

The halides (V), which are also required as starting materials, are known from the literature and can be prepared easily, even on an industrial scale.

As examples thereof, the following may be mentioned: methyl iodide, ethyl iodide, methyl bromide, ethyl bromide, allyl bromide, propargyl bromide, chloroacetic acid ethyl ester, bromoacetic acid ethyl ester, chloroacetonitrile, acetyl chloride, O,O-dimethyl-, -diethyl- and -dipropylphosphoric and -thionophosphoric acid ester chlorides, dimethylcarbamoyl chloride, diethylcarbamoyl chloride, methanesulfonic acid chloride and ethanesulfonic acid chloride.

Examples of phosphorylated 1,6-dihydro-3-hydroxy-6-oxo-pyridazine derivatives (IV) to be employed according to the process are: O-methyl-S-methyl-, O-methyl-S-ethyl-, O-methyl-S-n-propyl-, O-methyl-S-isopropyl-, O-methyl-S-n-butyl-, O-methyl-S-tert.-butyl-, O-ethyl-S-ethyl-, O-ethyl-S-n-propyl-, O-ethyl-S-isopropyl-, O-ethyl-S-n-butyl-, O-ethyl-S-sec.-butyl-, O-n-propyl-S-ethyl-, O-n-propyl-S-isopropyl-, O-butyl-S-n-propyl-, O-methoxyethyl-S-ethyl-, O-ethoxyethyl-S-n-propyl-, O-ethoxyethyl-S-n-butyl- and O-n-propoxyethyl-S-isopropyl-S-[1,6-dihydro-3-hydroxy-6-oxo-pyridazin-(1)ylmethyl]-dithiolphosphoric acid ester, the corresponding thiono compounds and the 4,5-di-halogen-substituted derivatives, and O-methyl-N-methyl-, O-methyl-N-ethyl-, O-methyl-N-n-propyl-, O-methyl-N-isopropyl-, O-ethyl-N-ethyl-, O-ethyl-N-n-propyl-, O-ethyl-N-isopropyl-, O-ethyl-N-n-butyl-, O-ethyl-N-allyl-, O-ethyl-N-propargyl-, O-n-propyl-N-ethyl-, O-isopropyl-N-ethyl- and O-isopropyl-N-n-propyl-S-[1,6-dihydro-3-hydroxy-6-oxo- and 1,6-dihydro-3-hydroxy-4,5-dichloro- or -dibromo-6-oxo-pyridazin-(1)ylmethyl]-thiolphosphoric acid ester-amide, the corresponding thiono compounds and the unsubstituted amides, and also O-methyl-, O-ethyl-, O-n-propyl-, O-isopropyl-, O-n-butyl-, O-sec.-butyl-, O-tert.-butyl-, O-ethoxymethyl-, O-ethoxyethyl-, O-n-propoxyethyl-S-[1,6-dihydro-3-hydroxy-6-oxo- and 1,6-dihydro-3-hydroxy-4,5-dichloro- or -dibromo-6-oxo-pyridazin-(1)ylmethyl]-methane- and -ethane-, -n-propane-, -isopropane- and -benzene-thiolphosphonic acid esters, as well as the corresponding thiono compounds and 1-oxo-4-hydroxyphthalazine derivatives.

Suitable solvents and diluents an optionally be co-used in the preparative process. Practically any inert organic solvent can be used for this purpose, especially aliphatic and aromatic, optionally chlorinated, hydrocarbons, such as benzene, toluene, xylene, benzine, methylene chloride, chloroform, carbon tetrachloride and chlorobenzene; ethers, such as diethyl ether, dibutyl ether and dioxane; ketones, for example acetone, methyl ethyl ketone, methylisopropyl ketone and methylisobutyl ketone; nitriles, such as acetonitrile and propionitrile; and amides, such as dimethylformamide.

Practically all customary acid-acceptors can be used as acid-binding agents. Alkali metal carbonates and alkali metal alcoholates, such as sodium carbonate, potassium carbonate, sodium methylate, sodium ethylate, potassium methylate, potassium ethylate and potassium tert.-butylate, have proved particularly suitable.

The reaction temperature can be varied over a fairly wide range. In general, the reaction is carried out at between 0° and 100° C, preferably at from 20° to 50° C, and usually under normal pressure.

In carrying out the process, the starting materials are in most cases employed in an equimolar ratio, although in process variant (a), a slight excess of the phosphoric acid salt (III) may optionally be used.

In general, the starting material (III) - optionally in one of the solvents mentioned above - is added dropwise to the halogenomethylpyridazine compound (II) and the mixture is allowed to react for at least one hour thereafter, with warming if necessary. After cooling, the reaction mixture is poured into water and extracted by shaking with an organic solvent, for example benzene, and the organic phase is worked up in the usual manner, for example by washing, drying and distillation.

In process variant (b), the halide (V), in slight excess, is generally added dropwise to the phosphorylated pyridazine component (IV), optionally in one of the solvents mentioned above, and in the presence of an acid acceptor, and the mixture is left for at least one hour, if appropriate with warming, to complete the reaction. After cooling, the mixture is taken up in an organic solvent and the organic phase is worked up in the usual manner, for example by washing, drying and distillation.

The new compounds are in some cases obtained in the form of oils which cannot be distilled without decomposition but can be freed of the last volatile constituents by so-called "slight distillation", that is to say prolonged heating under reduced pressure to moderately elevated temperatures, and can be purified in this way. They are characterized by the refractive index. Some of the products are obtained in a crystalline form; in such cases, they can be characterized by their melting points.

As has already been mentioned, the new S-[1,6-dihydro-6-oxo-pyridazin(1)ylmethyl]-(thiono)-(di)-thiolphosphoric (phosphonic) acid ester and ester-amide derivatives are distinguished by an outstanding insecticidal, including soil-insecticidal, acaricidal and nematicidal activity. They combine a low phytotoxicity with good action against both sucking and biting insects.

For this reason, the compounds according to the invention can be employed successfully as pesticides in plant protection and in the fields of hygiene and the protection of stored products.

To the sucking insects there belong, in the main, aphids (*Ahididae*) such as the green each aphid (*Myzus persicae*), the bean aphid (*Doralis fabae*), the bird cherry aphid (*Rhopalosiphum padi*), the pea aphid (*Macrosiphum pisi*) and the potato aphid (*Macrosiphum solanifolii*), the currant gall aphid (*Cryptomyzus korschelti*), the rosy apple aphid (*Sappaphis mali*), the mealy plum aphid (*Hyalopterus arundinis*) and the cherry black-fly (*Myzus cerasi*); in addition, scales and mealybugs (*Coccina*), for example the oleander scale (*Aspidiotus hederae*) and the soft scale (*Lecanium hesperidum*) as well as the grape mealybug (*Pseudococcus maritimus*); thrips (*Thysanoptera*), such as *Hercinothrips femoralis*, and bugs, for example the beet bug (*Piesma quadrata*), the red cotton bug (*Dysdercus intermedius*), the bed bug (*Cimex lectularius*), the assassin bug (*Rhodnius prolixus*) and Chagas' bug (*Triatoma infestans*) and, further, cicadas, such as *Euscelis bilobatus* and *Nephotettix bipunctatus*.

In the case of the biting insects, above all there should be mentioned butterfly caterpillars (*Lepidoptera*) such as the diamond-back moth (*Plutella maculipennis*), the gypsy moth (*Lymantria dispar*), the brown-tail moth (*Euproctis chrysorrhoea*) and tent caterpillar (*Malacosoma neustria*); further, the cabbage moth (*Mamestra brassicae*) and the cutworm (*Agrotis segetum*), the large white butterfly (*Pieris brassicae*), the small winter moth (*Cheimtobia brumata*), the green oak tortrix moth (*Tortrix viridana*), the fall armyworm (*Laphygma fruginerda*) and cotton worm (*Prodenia litura*), the ermine moth (*Hyponomeuta padella*), the Meditterranean flour moth (*Ephestia kuhniella*) and greater wax moth (*Galleria mellonella*).

Also to be classed with the biting insects are beetles (*Coleoptera*), for example the granary weevil (*Sitophilus granarius = Calandra granaria*), the Colorado beetle (*Leptinotarsa decemlineata*), the dock beetle (*Gastrophysa viridula*), the mustard beetle (*Pheedon cochleariae*), the blossom beetle (*Meligethes aeneus*), the raspberry beetle (*Byturus tomentosus*), the bean weevil (*Bruchidius = Acanthoscelides obtectus*), the leather beetle (*Dermestes frischi*), the khapra beetle (*Trogoderma granarium*), the flour beetle (*Tribolium castaneum*), the northern corn billbug (*Calandra* or *Sitophilus zeamais*), the drugstore beetle (*Stegobium paniceum*), the yellow mealworm (*Tenebrio molitor*) and the saw-toothed grain beetle (*Oryzaephilus surinamensis*), and also species living in the soil, for example wireworms (*Agriotes spec.*) and larvae of the cockchafer (*Melolontha melolontha*); cockroaches, such as the German cockroach (*Blattella germanica*), American cockroach (*Periplaneta americana*), Madeira cockroach (*Leucophaea* or *Rhyparobia maderae*), oriental cockroach (*Blatta orientalis*), the giant cockroach (*Blaberus giganteus*) and the black giant cockroach (*Blaberus fuscus*) as well as Henschoutedenia flexivitta; further *Orthoptera*, for example the house cricket (*Gryllus domesticus*); termites such as the eastern subterranean termite (*Reticulitermes flavipes*) and Hymenoptera such as ants, for example the garden ant (*Lasius niger*).

The Diptera comprise essentially the flies, such as the vinegar fly (*Drosophila melanogaster*), the Mediterranean fruit fly (*Ceratitis capitata*), the house fly (*Musca domestica*), the little house fly (*Fannia canicularis*), the black blow fly (*Phormia regina*) and bluebottle fly (*Calliphora erythrocephala*) as well as the stable fly (*Stomoxys calcitrans*); further, gnats, for example mosquitoes such as the yellow fever mosquito (*Aedes aegypti*), the northern house mosquito (*Culex pipiens*) and the malaria mosquito (*Anopheles stephensi*).

with the mites (*Acarina*) there are classed, in particular, the spider mites (*Tetranychidae*) such as the twospotted spider mite (*Tetranychus urticae*) and the European red mite (*Paratetranychus pilosus = Panonychus ulmi*), gall mites for example the blackcurrant gall mite (*Eriophyes ribis*) and tarsonemids, for example the broad mite (*Hemitarsonemus latus*) and the cyclamen mite (*Tarsonemus palidus*); finally, ticks, such as the relapsing fever tick (*Ornithodorus moubata*).

When applied against pests harmful to health and pests of stored products, particularly flies and mosquitoes, the process proucts are also distinguished by an outstanding residual activity on wood and clay, as well as a good stability to alkali on limed substrates.

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, suspensions, emulsifiable concentrates, spray powders, pastes, soluble powders, dusting agents, granules, etc. These are prepared in known manner, for instance by extending the active compounds with conventional pesticide dispersible liquid diluent carriers and/or dispersible solid carriers optionally with the use of carrier vehicle assistants, e.g. conevntional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose; aerosol propellants which are gaseous at normal temperatures and pressures, such as freon; inert disersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.) amides (e.g. dimethyl formamide, etc.), sulfoxides (e.g. dimethyl sulfoxide, etc.), acetonitrile, ketones (e.g. acetone, methyl ethyl ketone, methyl isobutyl ketone, cyclohexanone, etc.), and/or water; as well as inert dispersible finely divided solid carriers, such as ground natural minerals (e.g. kaolins, clays, alumina, silica, chalk, i.e. calcium carbonate, talc, attapulgite, montmorillonite, kieselguhr, etc.) and ground synthetic minerals (e.g. highly dispersed silicic acid, silicates, e.g. alkali silicates, etc.); whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as liqnin, sulfite waste liquors, methyl cellulose, etc.

such active compounds may be employed alone or in the form of mixtures with one another and/or with such solid and/or liquid dispersible carrier veicles and/or with other known compatible active agents, espcially plant protection agents, such as other insecticides, acaricides and nematocides, or fungicides, bactericides, rodenticides, herbicides, fertilizers, growth-regulating agents, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.0001–10%, preferably 0.01–1%, by weight of the mixture. Thus, the present invention contemplates over-all compositions which comprises mixtures of a conventional dispersible carrier vehicle such as (1) a dispersible inert finely divided carrier solid. and/or (2) a dispersible carrier liquid such as an inert organic solvent and/or water preferably including a surface-active effective amount of a carrier vehicle assistant, e.g. & surface-active agent, such as an emulsifying agent and/or a dispersing agent, and an amount of the active compound which is effective for the purpose in question and which is generally between about 0.0001–95%, and preferably 0.01–95%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

Furthermore, the present invention contemplates methods of selectively killing, combating or controlling pests, e.g. insects, acarids and nematodes, which comprises applying to at least one of correspondingly (a) such insects, (b) such acarids, (c) such nematodes, and (d) the corresponding habitat thereof, i.e. the locus to be protected, a correspondingly combative or toxic amount, i.e. an insecticidally, acaricidally or nematocidally effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, dressing, encrusting, and the like.

It will be realized, of course, that the concentration of the particular active compound utilized in admixture with the carrier vehicle will depend upon the intended application. Therefore, in special cases it is possible to go above or below the aforementioned concentration ranges.

The synthesis, unexpected superiority and outstanding activity of the particular new compounds of the present invention are illustrated, without limitation, by the following examples:

EXAMPLE 1

The 1,6-dihydro-1-halogenomethyl-6-oxo-pyridazines (II) to be used as starting materials can be prepared according to the following processes:

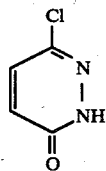
(a)

300 g (2.67 moles) of maleic acid hydrazide in 3 l or phosphorus oxychloride were boiled for 3 hours under reflux; the excess phosphorus oxychloride was then stripped off under reduced pressure. The oily residue was added dropwise to 1 liter of concentrated hydrochloric acid and the mixture was boiled for 1 hour under reflux and then poured into 2 l of water. On cooling, 300 g (87% of theory) of 1,6-dihydro-3-chloro-6-oxo-pyridazine of melting point 100° C separated out.

The following compounds of the general formula (VIII) listed in Table 1 can be prepared analogously:

Table 1

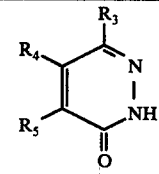
(VII)

| $R_3$ | $R_4$ | $R_5$ | Melting Point | Yield (% of theory) |
|---|---|---|---|---|
| Cl | Cl | Cl | m.p. 184° C | 76 |
| Cl | | | m.p. 272–274° C | 81 |

(b)

and (Isomer mixture)

44 g (0.27 mole) of 3,6-dichloro-4-methylpyridazine (prepared according to R. H. Mizzoni and P. E. Spoerri, J. Amer. Chem. Soc. 73 [1951], page 1,873) in 440 ml of 3.3 N sodium hydroxide solution were boiled for 3 hours under reflux and the mixture was then acidified hot with approximately 130 ml of 50% strength acetic acid. On cooling, 33 g (85% of theory) of the isomer mixture of the above formula, of melting point 147° C, crystallized out.

Analogously, 1,6-dihydro-3-bromo-6-oxo-pyridazine could be obtained from 3,6-dibromopyridazine (prepared according to J. Druey, K. Meier and K. Eichenberger, Helv. Chem. Acta 37 [1954], page 121) in a yield of 40% of theory; melting point 158 to 161° C.

1,6-Dihydro-3-hydroxy-4,5-dichloro-6-oxo-pyridazine (melting point > 280° C) and 1,6-dihydro-3-hydroxy-4,5-dibromo-6-oxo-pyridazine (melting point > 250° C) were prepared, for example, according to R. H. Mizzoni and P. E. Spoerri, J. Amer. Chem. Soc. 73 [1951], page 1,873.

1,6-Dihydro-3-diethoxy-thionophosphoryloxy-6-oxo-pyridazine and 1,2-dihydro-1-oxo-4-diethoxy-thionophosphoryloxy-phthalazine were obtained, for example, in accordance with United States Patent Specification 2,759,938.

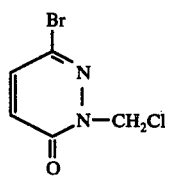
(c)

52.5 g (0.3 mole) of 1,6-dihydro-3-bromo-6-oxo-pyridazine and 150 ml of 30% strength formalin solution were heated to the boil for 30 minutes. After cooling, the precipitate which had separated out was filtered off and dried on clay and then taken up in 15 ml of methylene chloride. The solution was heated with 35.7 g (0.3 mole) of thionyl chloride for 2 hours under reflux, and the reaction mixture was then cooled, washed with saturated sodium bicarbonate solution and water, dried over sodium sulfate and evaporated. 49 g (69% theory) of 1,6-dihydro-2-chloromethyl-3-bromo-6-oxo-pyridazine were obtained to the form of colorless crystals of melting point 90° C.

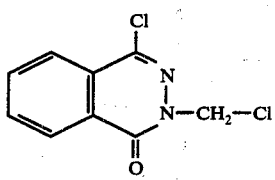
(d)

18 g (0.1 mole) of 4-chloro-1(2H-)phthalazone (prepared according to H. D. K. Drew and H. H. Hatt, J. Chem. Soc. 1937, page 16) in 125 ml of 30% strength formalin solution were heated for 5 hours under reflux. After cooling, the precipitate was filtered off, dried on clay and then introduced into 40 ml of thionyl chloride. The mixture was heated for 5 hours under reflux and the solvent was then stripped off. The oily residue which remained was boiled up in approximately 100 ml of chloroform. On cooling, 15 g (66% of theory) of 1-oxo-2-chloromethyl-4-chloro-phthalazine of melting point 142° C separated out.

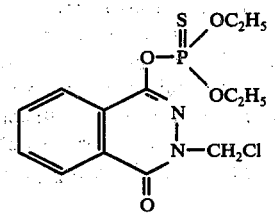
(e)

31.4 g (0.1 mole) of O,O-diethyl-O[1-oxo-phthalazin(-4)yl]-thionophosphoric acid ester in 80 ml of 30% strength formalin solution were heated to the boil for 10 minutes. After cooling, the precipitate was filtered off, dried on clay and then taken up in 100 ml of carbon tetrachloride. The solution was heated with 14.3 g (0.12 mole) of thionyl chloride for 2 hours to 70° C, and the mixture was cooled, washed with saturated sodium bicarbonate solution and water, dried over sodium sulfate and then evaporated. 24 g (61% of theory) of O,O-diethyl-O-[1-oxo-2-chloromethylphthalazin(4)yl]-thionophosphoric acid ester were obtained in the form of colorless crystals of melting point 53° C.

The following compounds of the general formula (II), listed in Table 2, could be obtained analogously:

Table 2

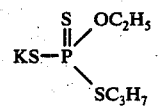
(II)

| Hal | R₃ | R₄ | R₅ | Physical constants (refractive index; melting point) | Yield (% of theory) |
|---|---|---|---|---|---|
| Cl | Cl | H | H | m.p. 72–74° C | 75 |
| Cl | Cl | H | CH₃ | m.p. 78–80° C | 48 |

Table 2-continued (II)

| Hal | R₃ | R₄ | R₅ | Physical constants (refractive index; melting point) | Yield (% of theory) |
|---|---|---|---|---|---|
| Cl | Cl | CH₃ | H | — | 91 |
| | | Cl | Cl | | |
| Cl | S‖C—P(OC₂H₅)₂ | H | H | $n_D^{26}$: 1.5306 | 65 |
| Cl | OH | H | H | m.p. 128° C | 60 |
| Cl | OH | Br | Br | m.p. 185° C | 66 |
| Cl | OH | Cl | Cl | — | 45 |

EXAMPLE 2

The salts of (thiono)(di)thiolphosphoric(phosphonic) acid esters and ester-amides to be employed in the process of the invention could be obtained by the following methods:

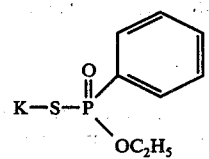

190 g of hydrogen sulfide were introduced over the course of 2 hours into a suspension of 280 g of potassium carbonate and 1.5 l of acetonitrile at 0° to 10° C. 218.5 g (1 mole) of O-ethyl-S-n-propyl-thionothiolphosphoric acid ester chloride were then added dropwise to the reaction mixture over the course of 20 minutes at the same temperature and the mixture was stirred for a further 18 hours at room temperature. Thereafter, a further 50 of H₂S were introduced at 0° to 10° C. The mixture was thereafter stirred for 48 hours at room temperature and the precipitate which had separated out was then filtered off and the filter residue was extracted by boiling with 1.5 l of acetone. After again filtering, the combined filtrates were freed of the solvent under reduced pressure. On adding ether, 125 g (50% of theory) of the salt of the above formula crystallized out.

(b)

729 g (3.3 moles) of O-ethyl-benzene-thionophosphonic acid ester chloride were dissolved in 1 liter of ethanol and 200 ml of water and 400 g of potassium hydroxide in 750 ml of water were added at a temperature below 70° C. The mixture was stirred for a further hour without cooling and the solvent was then removed under reduced pressure. The residue was dissolved in 1.5 l of ethanol, the potassium chloride which had precipitated was filtered off and the solvent was again stripped off. 770 g (97% of theory) of the potassium salt of O-ethyl-benzene-thiolphosphonic acid ester remained.

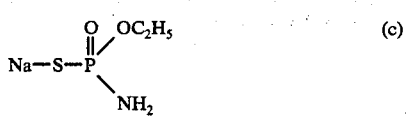

400 g (2.35 moles) of O,O-diethyl-thionophosphoric acid ester-amide were added dropwise to a solution of 94 g of sodium hydroxide in 680 ml of ethanol at 35° to 40° C. The mixture was stirred for 18 hours at room temperature and 50 ml of water were then added at 5° C. 300 g (64% of theory) of the sodium salt of O,O-ethyl-thiolphosphoric acid ester-amide were thus obtained.

The compounds were characterized by elementary analysis and NMR-spectrum.

The following compounds of the general formula (III), listed in Table 3, could be obtained in an analogous manner to that described above:

Table 3

$$M-S-P\begin{matrix}X\\||\\\end{matrix}\begin{matrix}OR_1\\ \\R_2\end{matrix} \quad (III)$$

| $R_1$ | $R_2$ | X | M | Preparation according to |
|---|---|---|---|---|
| $C_2H_5$ | $CH_3$ | S | K | a) |
| i-$C_3H_7$ | $CH_3$ | S | K | a) |
| $C_2H_5$ | $C_2H_5$ | S | K | a) |
| $C_2H_5$ | phenyl | S | K | a) |
| $C_2H_5$ | $SC_3H_7$ | O | K | b) |
| $C_2H_5$ | NH—$CH_3$ | S | K | a) |
| $C_2H_5$ | NH—$CH_3$ | O | K | b) |
| i-$C_3H_7$ | NH—$CH_3$ | S | K | a) |
| $C_2H_5$ | NH—$C_2H_5$ | S | K | a) |
| $C_2H_5$ | NH—$C_3H_7$-i | S | K | a) |
| $C_2H_5$ | NH—$C_3H_7$-i | O | K | b) |
| $C_2H_5$ | NH—$CH_2$—CH=$CH_2$ | S | K | a) |
| $CH_3O$—$CH_2$—$CH_2$ | NH—$C_3H_7$-i | S | K | a) |
| i-$C_3H_7$ | NH—$C_3H_7$-i | S | K | a) |
| $C_2H_5$ | NH—$C_4H_9$-n | S | K | a) |
| $C_2H_5$ | NH—$C_4H_9$-sec. | S | K | a) |

EXAMPLE 3

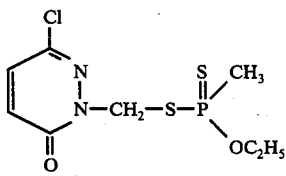

17.4 g (0.1 mole) of the potassium salt of O-ethyl-methanethionothiolphosphonic acid ester in 75 ml of acetonitrile were added to 17.9 g (0.1 mole) of 1,6-dihydro-1-chloromethyl-3-chloro-6-oxo-pyridazine in 75 ml of acetonitrile and the mixture was warmed to 50° C for 3 hours. The reaction mixture was then poured into water and the organic phase was taken up in methylene chloride and dried over sodium sulfate. After stripping off the solvent under reduced pressure, 17.6 g (90% of theory) of O-ethyl-methane-S-[1,6-dihydro-3-chloro-6-oxo-pyridazin(1)ylmethyl]-thionothiolphosphonic acid ester, having a refractive index $n_D^{25}$ of 1.5901, were obtained.

EXAMPLE 4

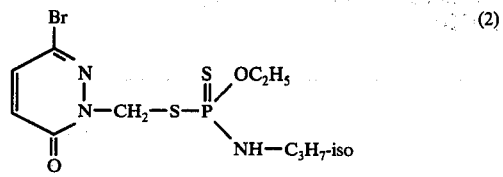

A mixture of 22.4 g (0.1 mole) of 1,6-dihydro-1-chloromethyl-3-bromo-6-oxo-pyridazine and 26.2 g (0.11 mole) of the potassium salt of O-ethyl-N-isopropyl-thionothiolphosphoric acid ester-amide in 100 ml of acetonitrile was heated to 50° C for 3 hours, the reaction mixture was poured into 500 ml of benzene and the benzene solution was washed with saturated sodium bicarbonate solution and water, dried over sodium sulfate and then evaporated. 32 g (82.5% of theory) of O-ethyl-N-isopropyl-S-[1,6-dihydro-3-bromo-6-oxo-pyradizin(1)-ylmethyl]-thionothiolphosphoric acid ester-amide were obtained as a yellow oil having a refractive index $n_D^{25}$ of 1.5902.

EXAMPLE 5

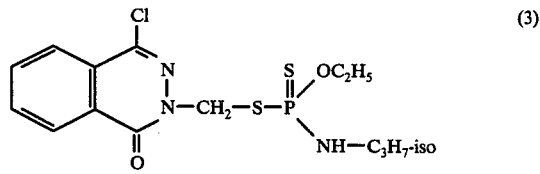

A mixture of 22.9 g (0.1 mole) of 2-chloromethyl-4-chlorophthalazone(1) and 26.2 g (0.11 mole) of the potassium salt of O-ethyl-N-isopropyl-thionothiolphosphoric acid ester-amide in 100 ml of acetonitrile was heated to 50° C for 3 hours. The reaction mixture was then taken up in 500 ml of benzene and the organic phase was washed with saturated sodium bicarbonate solution and water, dried over sodium sulfate and then evaporated. 32 g (82% of theory) of O-ethyl-N-isopropyl-S-[1-oxo-4-chloro-phthalazin(2)ylmethyl]-thionothiolphosphoric acid ester-amide were obtained in the form of colorless crystals of melting point 82° C.

EXAMPLE 6

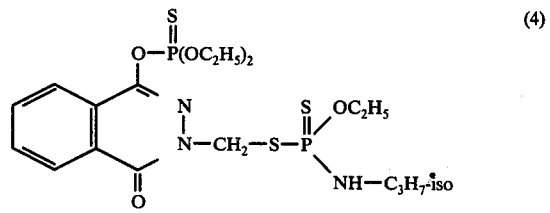

A mixture of 39.3 g (0.1 mole) of O,O-diethyl-O-[1-oxo-2-chloromethyl-phthalazin(4)yl]-thionophosphoric acid ester and 26.2 g (0.11 mole) of the potassium salt of O-ethyl-N-isopropyl-thionothiolphosphoric acid ester-amide in 150 ml of acetonitrile was heated to 40° C for 4 hours. After cooling, the reaction mixture was taken up in 500 ml of benzene and the organic phase was washed with saturated sodium bicarbonate solution and water, dried over sodium sulfate and then evaporated. 44 g (84% of theory) of O-ethyl-N-isopropyl-S-[1-oxo- 4-diethoxythionophosphoryloxy-phthalazin(2)ylmethyl]-thionothiolphosphoric acid ester-amide were obtained as a yellow oil having a refractive index $n_D^{22}$ of 1.5710.

The following compounds of the general formula (I), listed in Table 4, could be obtained analogously:

Table 4

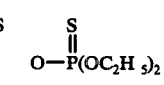
(I)

| Compound | $R_1$ | $R_2$ | X | $R_3$ | $R_4$ | $R_4$ | Physical constants refractive index; melting point | Yield (% of theory) |
|---|---|---|---|---|---|---|---|---|
| 5 | $C_2H_5$ | $C_2H_5$ | S | Cl | H | H | $n_D^{25}$: 1.5901 | 56.5 |
| 6 | $C_2H_5$ | 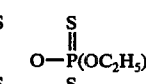 | S | Cl | H | H | $n_D^{25}$:1.6255 | 85 |
| 7 | $C_2H_5$ | 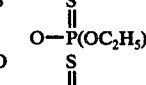 | O | Cl | H | H | $n_D^{25}$:1.5863 | 87.5 |
| 8 | $C_2H_5$ | $SC_3H_7$ | S | Cl | H | H | $n_D^{25}$:1.5962 | 56 |
| 9 | $C_2H_5$ | $SC_3H_7$ | O | Cl | H | H | $n_D^{25}$:1.5635 | 56 |
| 10 | $C_2H_5$ | $NH-CH_3$ | S | Cl | H | H | $n_D^{25}$:1.5970 | 63.6 |
| 11 | $C_2H_5$ | $NH-CH_3$ | O | Cl | H | H | $n_D^{25}$:1.5628 | 50 |
| 12 | $C_3H_7$-i | $NH-CH_3$ | S | Cl | H | H | m.p.91–93° C | 52 |
| 13 | $C_2H_5$ | $NH-C_2H_5$ | S | Cl | H | H | $n_D^{25}$:1.6540 | 49 |
| 14 | $C_2H_5$ | $NH-C_3H_7$-i | S | Cl | H | H | m.p.54° C | 82 |
| 15 | $C_2H_5$ | $NH-C_3H_7$-i | O | Cl | H | H | $n_D^{25}$:1.5453 | 98.5 |
| 16 | $C_2H_5$ | $NH-CH_2-CH=CH_2$ | S | Cl | H | H | $n_D^{25}$:1.5942 | 99 |
| 17 | $CH_2-CH_2-OCH_3$ | $NH-C_3H_7$-i | S | Cl | H | H | $n_D^{25}$:1.5755 | 27 |
| 18 | $C_3H_7$ | $NH-C_3H_7$-iso | S | Cl | H | H | $n_D^{25}$:1.5712 | 62 |
| 19 | $C_2H_5$ | $NH-C_4H_9$-iso | S | Cl | H | H | m.p.61° C | 67.5 |
| 20 | $C_2H_5$ | $NH-C_4H_9$-sec. | S | Cl | H | H | m.p.58° C | 73 |
| 21 | $C_2H_5$ | $SC_3H_7$ | S | Br | H | H | $n_D^{25}$:1.6077 | 68 |
| 22 | $C_2H_5$ | $NH-CH_3$ | S | Br | H | H | $n_D^{25}$:1.6047 | 86 |
| 23 | (Isomer mixture) | $C_2H_5$ | $NH-C_3H_7$-iso | S | Cl | H CH_3 | CH_3 H | m.p.100–101° C | 76 |
| 24 | " | $C_2H_5$ | $C_2H_5$ | S | Cl | H CH_3 | CH_3 H | $n_D^{25}$:1.5776 | 72 |
| 25 | " | $C_2H_5$ | $NH_2$ | O | Cl | H CH_3 | CH_3 H | $n_D^{25}$:1.5435 | 65 |
| 26 | i-$C_3H_7$ | $CH_3$ | S | Cl | Cl | Cl | $n_D^{25}$:1.5979 | 80 |
| 27 | $C_2H_5$ | $NH-C_3H_7$-iso | S | Cl | Cl | Cl | $n_D^{24}$:1.5936 | 73 |
| 28 | $C_2H_5$ | $C_2H_5$ | S | Cl | 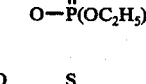 | | m.p. 82° C | 84 |
| 29 | $C_2H_5$ | $CH_3$ | S | Cl | 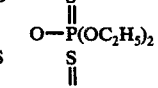 | | m.p. 94° C | 86 |
| 30 | $C_2H_5$ | $C_2H_5$ | S | $\begin{array}{c} S \\ \parallel \\ O-P(OC_2H_5)_2 \end{array}$ | 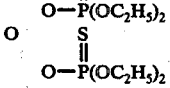 | | $n_D^{24}$:1.5741 | 65 |
| 31 | $C_3H_7$-i | $CH_3$ | S | $\begin{array}{c} S \\ \parallel \\ O-P(OC_2H_5)_2 \end{array}$ | H | H | $n_D^{25}$:1.5522 | 87 |
| 32 | $C_2H_5$ | $C_2H_5$ | S | $\begin{array}{c} S \\ \parallel \\ O-P(OC_2H_5)_2 \end{array}$ | H | H | $n_D^{25}$:1.5532 | 97 |
| 33 | $C_2H_5$ | 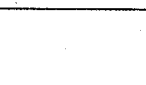 | O | $\begin{array}{c} S \\ \parallel \\ O-P(OC_2H_5)_2 \end{array}$ | H | H | $n_D^{25}$:1.5571 | 65 |
| 34 | $C_2H_5$ | $NH-C_3H_7$-iso | O | $\begin{array}{c} S \\ \parallel \\ O-P(OC_2H_5)_2 \end{array}$ | H | H | $n_D^{25}$:1.5258 | 80.9 |
| 35 | $C_2H_5$ | $NH-C_3H_7$-iso | S | $\begin{array}{c} S \\ \parallel \\ O-P(OC_2H_5)_2 \end{array}$ | H | H | $n_D^{25}$:1.5473 | 87.5 |
| 36 | $C_2H_5$ | $NH-CH_3$ | O | $\begin{array}{c} S \\ \parallel \\ O-P(OC_2H_5)_2 \end{array}$ | H | H | $n_D^{25}$:1.5359 | 79 |

EXAMPLE 7

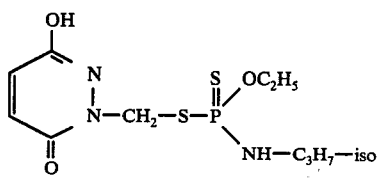
(37)

17.0 g (0.1 mole) of 2-chloromethyl-3-hydroxy-6-oxo-pyridizine in 100 ml of methyl isobutyl ketone were added to a suspension of 23.6 g (0.1 mole of the potassium salt of O-ethyl-N-isopropyl-thionothiolphosphoric acid ester-amide and 12,6 g of sodium bicarbonate in 150 ml of methyl isobutyl ketone. The mixture was warmed to 60° C for 2 hours, while stirring. After cooling, the mixture was freed of insoluble constituents, the filtrate was concentrated under reduced pressure and the residue was recrystallized from a 1:1 mixture of methanol and water. 15 g (47% of theory) of O-ethyl-N-isopropyl-S-[1,6-dihydro-3-hydroxy-6-oxo-pyridazin(1)yl-methyl]-thionothiolphosphoric acid ester-amide of melting point 156° C were obtained.

The following compounds of the general formula (IV), listed in Table 5, could be prepared analogously:

(0.11 mole) of O,O-dimethylthionophosphoric acid ester chloride were then added dropwise at 0° C. The mixture was stirred for 15 hours at room temperature and the salt which separated out was filtered off. The organic solution was washed with 10% strength potassium carbonate solution and subsequently with water until it gave a neutral reaction and was dried over sodium sulfate. Finally the solvent was stripped off under reduced pressure and the residue was subjected to "slight distillation". 33 g (74% of theory) of O-ethyl-N-isopropyl-S-[1,6-dihydro-3-dimethoxythionophosphoryloxy-6-oxo-pyridazin(1)ylmethyl]-thionothiolphosphoric acid ester-amide having a refractive index $n_D^{25}$ of 1.5610 were obtained.

EXAMPLE 9

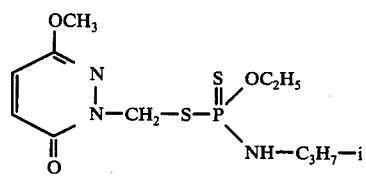
(46)

A mixture of 32.3 g (0.1 mole) of O-ethyl-N-isopropyl-S-[1,6-dihydro-3-hydroxy-6-oxo-pyridazin(1)ylme-

Table 5

(IV)

| Compound | $R_1$ | $R_2$ | X | $R_4$ | $R_5$ | Physical constants (refractive index; melting point) | Yield (% of theory) |
|---|---|---|---|---|---|---|---|
| 38 | $C_3H_7$-iso | $CH_3$ | S | H | H | m.p.162° C | 66 |
| 39 | $C_2H_5$ | $NH-C_2H_5$ | S | H | H | m.p.150° C | 57 |
| 40 | $C_2H_5$ | $NH-CH_3$ | S | H | H | m.p.175° C | 80 |
| 41 | $C_2H_5$ | $C_2H_5$ | S | Br | Br | m.p.105° C | 81 |
| 42 | $C_3H_7$-iso | $CH_3$ | S | Br | Br | $n_D^{25}$: 1.6150 | 78 |
| 43 | $C_2H_5$ | $NH-C_3H_7-$ | S | Br | Br | m.p.120° C | 50 |
| 44 | $C_2H_5$ | $NH-C_3H_7$-i | S | Cl | Cl | m.p. 130° C | 60 |

EXAMPLE 8

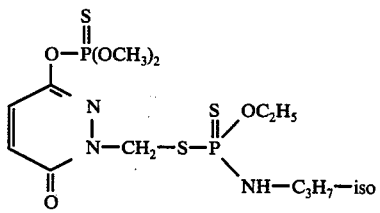
(45)

A mixture of 32.3 g (0.1 mole) of O-ethyl-N-isopropyl-S-[1,6-dihydro-3-hydroxy-6-oxo-pyridazin(1)ylmethyl]-thionothiolphosphoric acid ester-amide (melting point 156° C; described in Example 7) in methyl isobutyl ketone and 11.2 g (0.1 mole) of finely powdered potassium tert.-butylate was stirred for 1 hour, and 17.7 g thyl]-thionothiolphosphoric acid ester-amide (described in Example 37), in 200 ml of methyl isobutyl ketone and 11.2 g (0.1 mole) of potassium tert.-butylate was stirred until a clear homogeneous solution had been produced. After adding 15.6 g (0.11 mole) of methyl iodide, the mixture was stirred for a further 3 hours at 45° C and, after cooling, it was washed with 100 ml of water, 100 ml of 10% strength sodium hydroxide solution and 100 ml of water and dried over sodium sulfate. The solvent was stripped off under reduced pressure and the residue was subjected to "slight distillation". 27 g (80% of theory) of O-ethyl-N-isopropyl-S-[1,6-dihydro-3-methoxy-6-oxo-pyridazin(1)ylmethyl]-thionothiolphosphoric acid ester-amide having a refractive index $n_D^{25}$ of 1.5593 were obtained.

The following compounds of the general formula (I), listed in Table 6, could be prepared analogously:

Table 6

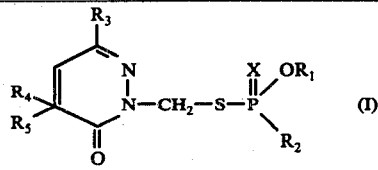

| Compound | $R_1$ | $R_0$ | X | $R_3$ | $R_4$ | $R_5$ | Physical constants (refractive index; melting point) | Yield (% of theory) |
|---|---|---|---|---|---|---|---|---|
| 47 | $C_3H_7$-i | $CH_3$ | S | $OCH_3$ | H | H | m.p.55–56° C | 76.4 |
| 48 | $C_2H_5$ | $NH-C_2H_5$ | S | $OCH_3$ | H | H | m.p.51° C | 77.5 |
| 49 | $C_2H_5$ | $NH-CH_3$ | S | $OCH_3$ | H | H | m.p.72° C | 76 |
| 50 | $C_2H_5$ | $NH-C_3H_7$-i | S | $O-CH_2-C\equiv CH$ | H | H | $n_D^{25}$: 1.5619 | 47 |
| 51 | $C_2H_5$ | $NH-C_3H_7$-i | S | $O-CH_2-CH=CH_2$ | H | H | $n_D^{25}$: 1.5573 | 66 |
| 52 | $C_2H_5$ | $NH-C_3H_7$-i | S | $O-CH_2-CO-OC_2H_5$ | H | H | $n_D^{25}$: 1.5426 | 80.6 |
| 53 | $C_2H_5$ | $NH-C_3H_7$-i | S | $O-CH_2-CN$ | H | H | $n_D^{25}$: 1.5525 | 22 |
| 54 | $C_2H_5$ | $NH-C_3H_7$-i | S | $O-CH_3$ | Br | Br | m.p.116° C | 34.5 |
| 55 | $C_3H_7$-i | $CH_3$ | S | $O-CH_3$ * | Br | Br | $n_P^{25}$: 1.5945 | 25.5 |
| 56 | $C_2H_5$ | $C_2H_5$ | S | $O-CH_3$ | Br | Br | $n_D^{25}$: 1.5892 | 36 |
| 57 | $C_2H_5$ | $NH-C_3H_7$-i | S | $O-CH_3$ | Cl | Cl | m.p. 98–100° C | 33 |
| 58 | $C_2H_5$ | $NH-C_3H_7$-i | S | $O-CO-CH_3$ | H | H | m.p. 74° C | 41 |
| 59 | $C_2H_5$ | $NH-C_3H_7$-i | S | $O-CO-N(CH_3)_2$ | H | H | $n_D^{25}$: 1.5620 | 50 |
| 60 | $C_2H_5$ | $NH-C_3H_7$-i | S | $O-SO_2-CH_3$ | H | H | m.p. 85° C | 67.5 |

The pesticidal activity of the compounds of this invention is illustrated in the following test examples. The active compounds of this invention are identified by the same numbers as in preparative examples hereinabove.

EXAMPLE 10

Phaedon larvae test
Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier and the concentrae was diluted with water to the desired concentration.

Cabbage plants (*Brassica cleracea*) were sprayed with the preparation of the active compound until dripping wet and were then infested with mustard beetle larvae (*Phaedon cochleariae*).

After the specified periods of time, the degree of destruction was determined in %: 100% means that all beetle larvae were killed whereas 0% means that none of the beetle larvae were killed.

The active compounds, the concentrations, by weight, of the active compounds, the evaluation times and the results can be seen from the following table:

Table 7
(Phaedon larvae test)

| Active compound | Active compound concentration in % | Degree of destruction in % after 3 days |
|---|---|---|
| ![structure] Cl-pyridazinone-N-CH₂S-P(S)(OC₃H₇i)₂ (known) (D) | 0.1 | 80 |
| | 0.01 | 0 |

Table 7-continued
(Phaedon larvae test)

| Active compound | Active compound concentration in % | Degree of destruction in % after 3 days |
|---|---|---|
| CH₃O-pyridazinone-N-CH₂S-P(S)(OC₂H₅)₂ (known) (B) | 0.1 | 100 |
| | 0.01 | 0 |
| (1) | 0.1 | 100 |
| | 0.01 | 100 |
| (5) | 0.1 | 100 |
| | 0.01 | 100 |
| (8) | 0.1 | 100 |
| | 0.01 | 100 |
| (9) | 0.1 | 100 |
| | 0.01 | 100 |
| (10) | 0.1 | 100 |
| | 0.01 | 100 |
| (11) | 0.1 | 100 |
| | 0.01 | 100 |
| (13) | 0.1 | 100 |
| | 0.01 | 100 |
| (14) | 0.1 | 100 |
| | 0.01 | 100 |
| (15) | 0.1 | 100 |
| | 0.01 | 100 |
| (19) | 0.1 | 100 |
| | 0.01 | 100 |
| | 0.001 | 60 |
| (20) | 0.1 | 100 |
| | 0.01 | 100 |
| | 0.001 | 30 |
| (16) | 0.1 | 100 |
| | 0.01 | 100 |
| (18) | 0.1 | 100 |
| | 0.01 | 100 |
| (24) | 0.1 | 100 |
| | 0.01 | 100 |
| (23) | 0.1 | 100 |
| | 0.01 | 90 |
| (21) | 0.1 | 100 |
| | 0.01 | 100 |
| (22) | 0.1 | 100 |
| | 0.01 | 100 |
| (48) | 0.1 | 100 |
| | 0.01 | 80 |
| (46) | 0.1 | 100 |
| | 0.01 | 100 |
| (29) | 0.1 | 100 |
| | 0.01 | 100 |
| | 0.001 | 90 |
| (28) | 0.1 | 100 |
| | 0.01 | 100 |

Table 7-continued
(Phaedon larvae test)

| Active compound | Active compound concentration in % | Degree of destruction in % after 3 days |
|---|---|---|
| (3) | 0.001 | 70 |
| | 0.1 | 100 |
| | 0.01 | 100 |
| (31) | 0.001 | 45 |
| | 0.1 | 100 |
| | 0.01 | 100 |
| (32) | 0.001 | 70 |
| | 0.1 | 100 |
| | 0.01 | 100 |
| (33) | 0.1 | 100 |
| | 0.01 | 90 |
| (36) | 0.1 | 100 |
| | 0.01 | 85 |
| (45) | 0.1 | 100 |
| | 0.01 | 100 |
| (35) | 0.1 | 100 |
| | 0.01 | 100 |
| (34) | 0.1 | 100 |
| | 0.01 | 95 |

EXAMPLE 11

Myzus test (contact action)

Solvent: 3 parts by weight of acetone

Emulsifier: 1 part by weight of alkylaryl polyglycol ether

To produce a suitable preparation of active compound, 1 part by weight of the active compound was mixed with the stated amount of solvent containing the stated amount of emulsifier and the concentrate was diluted with water to the desired concentration.

Cabbage plants (*Brassica oleracea*) which had been heavily infested with peach aphids (*Myzus persicae*) were spayed with the preparation of the active compound until dripping wet.

After the specified periods of time, the degree of destruction was determined as a percentage: 100% means that all the aphids were killed whereas 0% means that noen of the aphids were killed.

The active compounds, the concentrations, by weight, of the active compounds, the evaluation times and the results can be seen from the following table:

Table 8
(*Myzus* test)

| Active compound | Active compound concentration in % | Degree of destruction in % after 1 day |
|---|---|---|
| (B) (known) CH₃O–...–N–CH₂S–P(OC₂H₅)₂ (with O, S, N ring) | 0.1 | 100 |
| | 0.01 | 100 |
| | 0.001 | 0 |
| (E) (known) Cl–C₆H₄–...–N–CH₂S–P(OC₂H₅)₂ | 0.1 | 100 |
| | 0.01 | 80 |
| | 0.001 | 30 |
| (C) (known) (C₂H₅O)₂P(S)–O–...=O, N–N, CH₂–S–P(OC₂H₅)₂ | 0.1 | 100 |
| | 0.01 | 90 |
| | 0.001 | 20 |
| (5) | 0.1 | 100 |
| | 0.01 | 100 |
| | 0.001 | 95 |
| (2) | 0.1 | 100 |
| | 0.01 | 100 |
| | 0.001 | 92 |
| | 0.0001 | 50 |
| (31) | 0.1 | 100 |
| | 0.01 | 100 |
| | 0.001 | 95 |

EXAMPLE 12

Tetranychus test

Solvent: 3 parts by weight of acetone

Emulsifier: 1 part by weight of alkylaryl polyglycol ether

To produce a suitable preparation of active compound, 1 part by weight of the active compound was mixed with the stated amount of solvent containing the stated amount of emulsifier and the concentrate so obtained was diluted with water to the desired concentration.

Bean plants (*Phaseolus vulgaris*), which had a height of approximately 10–30 cm, were sprayed with the preparation of the active compound until dripping wet. These bean plants were heavily infested with the two-spotted spider mite (*Tetranychus urticae*) in all stages of development.

After the specified periods of time, the effectiveness of the preparation of active compound was determined by counting the dead mites. The degree of destruction thus obtained was expressed as a percentage: 100% means that all the spider mites were killed whereas 0% means that none of the spider mites were killed.

The active compounds, the concentrations, by weight, of the active compounds, the evaulation times and the results can be seen from the following table:

Table 9

(Tetranychus test)

| Active compound | Active compound concentration in % | Degree of destruction in % after 2 days |
|---|---|---|
| (known) (E) [structure: chlorobenzyl hydrazone with N—CH$_2$S—P(OC$_2$H$_5$)$_2$ group and C=O] | 0.1 | 0 |
| (known) (C) (C$_2$H$_5$O)$_2$P(S)—O—[pyridazinone]—N—N—CH$_2$—S—P(OC$_2$H$_5$)$_2$ | 0.1 | 40 |
| | 0.01 | 0 |
| (1) | 0.1 | 100 |
| | 0.01 | 100 |
| | 0.001 | 55 |
| (5) | 0.1 | 100 |
| | 0.01 | 100 |
| (9) | 0.1 | 100 |
| | 0.01 | 90 |
| (10) | 0.1 | 100 |
| | 0.01 | 99 |
| (11) | 0.1 | 100 |
| | 0.01 | 99 |
| (13) | 0.1 | 100 |
| | 0.01 | 100 |
| | 0.001 | 80 |
| (14) | 0.1 | 100 |
| | 0.01 | 100 |
| | 0.001 | 99 |
| | 0.0001 | 25 |
| (15) | 0.1 | 100 |
| | 0.01 | 100 |
| (20) | 0.1 | 100 |
| | 0.01 | 100 |
| (16) | 0.1 | 100 |
| | 0.01 | 100 |
| (18) | 0.1 | 100 |
| | 0.01 | 98 |
| (25) | 0.1 | 100 |
| | 0.01 | 75 |
| (21) | 0.1 | 100 |
| | 0.01 | 100 |
| | 0.001 | 97 |
| (22) | 0.1 | 100 |
| | 0.01 | 100 |
| (2) | 0.1 | 100 |
| | 0.01 | 98 |
| (47) | 0.1 | 100 |
| | 0.01 | 90 |
| (48) | 0.1 | 100 |
| | 0.01 | 100 |
| (46) | 0.1 | 100 |
| | 0.01 | 100 |
| | 0.001 | 45 |

EXAMPLE 13

Critical concentration test/soil insects
Test insect: Cabbage fly maggots (*Phorbia brassicae*)
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration. The preparation of active compound was intimately mixed with the soil. The concentration of the active compound in the preparation was practically immaterial, the only decisive factor being the amount by weight of active compound per unit volume of soil, which is quoted in ppm (for example mg/l). The soil was filled into pots and the pots were left to stand at room temperature. After 24 hours the test insects were introduced into the treated soil and after a further 48 hours the degree of effectiveness of the active compound was determined in % by counting the dead and livetest insects. The degree of effectiveness was 100% if all test insects were killed and was 0% if exactly as many test insects were still alive as in the case of the control.

The active compounds, amounts used and results can be seen from the table which follows:

Table 10

| | (Phorbia brassicae/maggots in soil) | | | |
|---|---|---|---|---|
| | Degree of destruction in % at an active compond concentration of | | | |
| Active compound | 20 | 10 | 5 | 2.5 ppm |
| (5) | 100 | 100 | 75 | |
| (1) | 100 | 100 | 50 | |
| (14) | 100 | 95 | 75 | |
| (21) | 100 | 95 | 50 | |
| (24) | 100 | 100 | 90 | 50 |
| (known) (A) | 100 | 80 | 0 | |
| (known) (C) | 90 | 20 | 0 | |

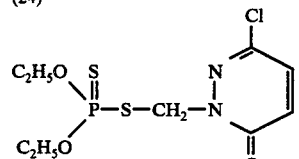

(known)    (A)

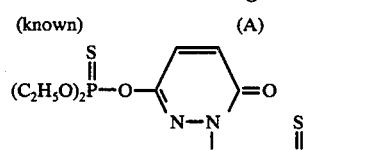

(known)    (C)

EXAMPLE 14

Critical concentration test/soil insects
Test insect: Tenebrio m. larvae in soil
Solvent: 3 parts by weight of acetone
Emulsfier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration. The preparation of active compound was intimately mixed with the soil. The concentration of the active compound in the preparation was practically immaterial, the only decisive factor being the amount by weight of active compound per unit volume of soil, which is quoted in ppm (for example mg/l). The soil was filled into pots and the pots were left to stand at room temperature. After 24 hours the test insects were introduced into the treated soil and after a further 48 hours the degree of effectiveness of the active compound was determined in % by counting the dead and live test insects. The degree of effectiveness was 100% if all test insects were killed and was 0% if exactly as many test insects were till alive as in the case of the control.

The active compounds, amounts used and results can be seen from the table which follows:

Table 11

| | (Tenebrio m. larvae in soil) | | | |
|---|---|---|---|---|
| | Degree of destruction in % at an active compond concentration of | | | |
| Active compound | 20 | 10 | 5 | 2.5 ppm |
| (5) | 100 | 90 | 70 | |
| (10) | 100 | 100 | 60 | |
| (13) | 100 | 100 | 70 | |
| (22) | 100 | 100 | 80 | 60 |
| (known) (A) | 100 | 70 | 0 | |
| (known) (C) | 0 | | | |

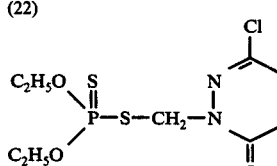

(known)    (A)

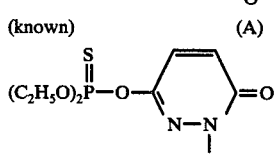

(known)    (C)

EXAMPLE 15

Critical concentration test
Test nematode: Meloidogyne incognita
Solvent: 3 parts by weight of acetone Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with soil which was heavily infested with the test nematodes. The concentration of the active compound in the preparation was of practically no importance; only the amount of active compound per unit volume of soil, which is given in ppm, was decisive. The soil was filld into pots, lettuce was sown therein and the pots were kept at a greenhouse temperature of 27° C. After 4 weeks, the lettuce roots were examined for infestation with nematodes, and the degree of effectiveness of the active compound was determined as a percentage. The degree of effectiveness was 100% when infestation had been completely avoided; it was 0% when the infestation was exactly the same as in the case of the control plants in untreated soil which had been infested in the same manner.

The active compound, the amounts applied and the results can be seen from the following table:

Table 12

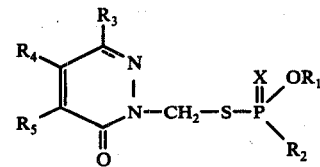

in which
- $R_1$ is alkyl or alkoxyalky having 1 to 6 carbon atoms per alkyl chain,
- $R_2$ is alkyl, alkylmercapto, alkylamino or alkenylamino having up to 6 carbon atoms per aliphatic chain, amino or phenyl,
- $R_3$ is alkoxy, cyanoalkoxy, carbalkoxy-alkoxy, alkenyloxy, alkynyloxy, alkanoyloxy, dialkylcarbamoyloxy or alkylsulfonyloxy having up to 5 carbon atoms in each aliphatic chain, halogen, hydroxyl, or a (thiono) (thiol)-phosphoric(phosphonic) acid ester or esteramide radical,
- $R_4$ and $R_5$ each independently is hydrogen, alkyl having 1 to 3 carbon atoms or halogen, or $R_4$ and $R_5$ conjointly form a fused benzene ring, and
- X is oxygen or sulfur.

| | (Meloidogyne incognita) | | | | |
|---|---|---|---|---|---|
| | Degree of destruction in % at an active compound concentration of | | | | |
| Active compound | 20 | 10 | 5 | 2.5 | 1.25 ppm |
| (5) | 100 | 95 | 50 | | |
| (14) | 100 | 100 | 100 | 98 | 95 |
| (15) | 100 | 100 | 100 | | |
| (20) | 100 | 99 | 97 | | |
| (10) | 100 | 100 | 100 | | |
| (13) | 100 | 100 | 99 | | |
| (18) | 100 | 100 | 99 | | |
| (22) | 100 | 100 | 99 | | |
| (21) | 100 | 100 | 99 | | |
| (23) | 100 | 98 | 70 | 40 | 0 |
| (A) | 98 | 95 | 0 | | |
| (C) | 0 | | | | |

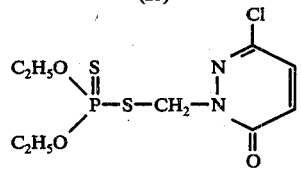

(known)  (A)

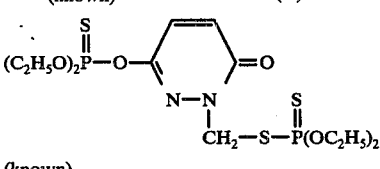

(known)  (C)

The process of this invention is illustrated in the following preparative Examples.

It will be appreciated that the instant specification and examples are set forth by way of illustration and not limitation, and that various modifications and changes may be made without departing from the spirit and scope of the present invention.

What is claimed is:

1. An S-[1,6-dihydro-6-oxo-pyridazin(1)ylmethyl]-(thiono)-(di)-thiol-phosphoric(phosphonic) acid ester of the formula 2. A compound according to claim 1, in which $R_1$ is alkyl or alkoxy-alkyl having 1 to 4 carbon atoms per alkyl chain, $R_2$ is alkyl, alkylmercapto, alkylamino or alkenylamino having up to 4 carbon atoms per aliphatic chain, amino or phenyl, $R_3$ is dialkoxy(thiono)-phosphoryloxy, alkanoyloxy, dialkylcarbamoyloxy, alkylsulfonyloxy, alkoxy, alkenyloxy, alkynyloxy or carbalkoxy-alkyloxy each having up to 3 carbon atoms per aliphatic chain, chlorine, bromine, hydroxyl or cyanomethyloxy, and $R_4$ and $R_5$ are each hydrogen, methyl, ethyl, chlorine or bromine, or conjointly denote a benzene ring.

3. The compound according to claim 1 wherein such compound is O-ethyl-S-propyl-S-[1,6-dihydro-3-chloro-6-oxo-pyridazin(1)ylmethyl]-thionodithiolphosphoric acid ester of the formula

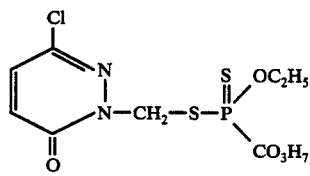

4. The compound according to claim 1 wherein such compound is O-ethyl-N-isopropyl-S-[1,6-dihydro-3-chloro-6-oxo-pyridazin(1)ylmethyl]-thionothiolphosphoric acid ester-amide of the formula

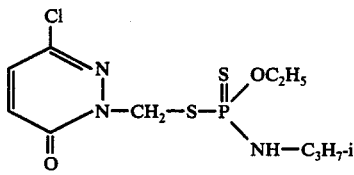

5. The compound according to claim 1 wherein such compound is O-ethyl-methane-S-[1-oxo-4-chloro-phthalazin-(2)ylmethyl]-thionothiolphosphonic acid ester of the formula

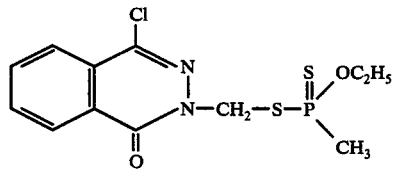

6. The compound according to claim 1 wherein such compound is O-isopropyl-methane-S-[1,6-dihydro-3-diethoxythionophosphoryloxy-6-oxo-pyridazin(1)ylmethyl]-thionothiolphosphonic acid ester of the formula

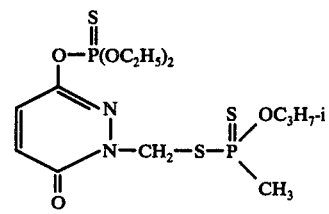

7. The compound according to claim 1 wherein such compound is O-ethyl-N-isopropyl-S-[1,6-dihydro-3-methoxy-6-oxo-pyridazin(1)ylmethyl]-thionothiolphosphoric acid ester-amide of the formula

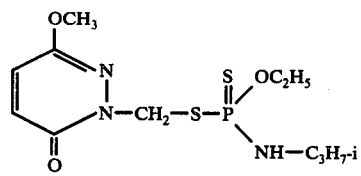

8. An insecticidal, acaricidal or nematicidal composition containing as active ingredient an insecticidally, acaricidally or nematocidally effective amount of a compound according to claim 1 in admixture with a diluent.

9. A method of combating insects, acarids or nematodes which comprises applying to Phaedon larvae, Myzus, Tetranychus urticae, Phorbia brassicae, Tenebrio m. larvae, Meloidogyne incognita, Rhopalosiphum, Drosophila melanogaster, Plutella or Euscelis bilobatus, or to a habitat thereof, an insecticidally, acaricidally or nematocidally effective amount of a compoun according to claim 1.

10. The method according to claim 1 in which said compound is
O-ethyl-S-propyl-S-[1,6-dihydro-3-chloro-6-oxo-pyridazin(1)ylmethyl]-thionodithiolphosphoric acid ester,
O-ethyl-N-isopropyl-S-[1,6-dihydro-3-chloro-6-oxo-pyridazin(1)ylmethyl]-thionothiolphosphoric acid ester-amide,
O-ethyl-methane-S-[1-oxo-4-chloro-phthalazin(2)-ylmethyl]-thionothiolphosphonic acid ester,
O-isopropyl-methane-S-[1,6-dihydro-3-diethoxythionophosphoryloxy-6-oxo-pyridazin(1)-ylmethyl]-thionothiolphosphonic acid ester, or
O-ethyl-N-isopropyl-S-[1,6-dihydro-3-methoxy-6oxo-pyridazin(1)ylmethyl]-thionothiolphosphoric acid ester-amide.

* * * * *

UNITED STATES PATENT AND TRADEMARK OFFICE
CERTIFICATE OF CORRECTION

PATENT NO. : 4,112,080                        Page 1 of 4
DATED : September 5, 1978
INVENTOR(S) : Hofer et al It is certified that error appears in the above-identified patent and that said Letters Patent are hereby corrected as shown below:

| | |
|---|---|
| Col. 1, line 23 | Delete "parts", substitute --pests--. |
| Col. 2, line 30 | Delete "ehtyl", substitute --ethyl--. |
| Col. 2, line 65 | Delete "reached", substitute --reacted--. |
| Col. 4, line 32 | Insert -- - -- after "4" before "dimethoxy". |
| Col. 6, line 47 | Delete "each", substitute --peach--. |
| Col. 7, line 4 | Delete "cak", substitute --oak--. |
| Col. 7, line 6 | Delete "fruginerda", substitute --frugiperda--. |
| Col. 7, line 7 | Delete "Meditter-", substitute --Mediter- --. |
| Col. 7, line 8 | Delete "Kuhniella", substitute --Kühniella--. |
| Col. 7, line 14 | Delete "Pheedon", substitute --Phaëdon--. |
| Col. 7, line 47 | Delete "with", substitute --With--. |
| Col. 7, line 54 | Delete "palidus", substitute --pallidus--. |
| Col. 7, line 58 | Delete "proucts", substitute --products-- |
| Col. 8, line 46 | Delete "such", substitute --Such--. |

UNITED STATES PATENT AND TRADEMARK OFFICE
CERTIFICATE OF CORRECTION

PATENT NO. : 4,112,080            Page 2 of 4
DATED : September 5, 1978
INVENTOR(S) : Hofer et al It is certified that error appears in the above-identified patent and that said Letters Patent are hereby corrected as shown below:

| | |
|---|---|
| Col. 8, line 48 | Delete "veicles", substitute --vehicles--. |
| Col. 8, line 49 | Delete "espcially", substitute --especially--. |
| Col. 9, line 5 | Delete "&", substitute --a--. |
| Col. 9, line 65 | Delete "or", substitute --of--. |
| Col. 11, line 2 | Delete "15", substitute --150--. |
| Col. 11, line 9 | Delete "to", substitute --in--. |
| Col. 12, line 39 | Insert --g-- after "50". |
| Col. 13, line 12 | Delete "0,", before "0-". |
| Col. 16, sub-col. 8, compound no. 30 | Delete "$n_D^{24}:1.5741$", substitute --$n_D^{4\ 22}:1.5741$--. |
| Col. 17, line 12 | Delete "pyridizine", substitute --pyridazine--. |
| Col. 17, line 15 | Delete "12,6", substitute --12.6--. |
| Col. 17, Table 5, compound 43, thrd. col. | Insert --i-- after "$C_3H_7$-". |

UNITED STATES PATENT AND TRADEMARK OFFICE
CERTIFICATE OF CORRECTION

PATENT NO. : 4,112,080　　　　　　　　　　　Page 3 of 4
DATED : September 5, 1978
INVENTOR(S) : Hofer et al It is certified that error appears in the above-identified patent and that said Letters Patent are hereby corrected as shown below:

| | |
|---|---|
| Col. 20, compd. 47, sub-column $R_5$ | Delete "11", substitute --H--. |
| Col. 19, comd. 58, column 3 | Delete "NH-$C_7$-i", substitute --NH-$C_3H_7$-i--. |
| Col. 19, line 41 | Delete "concentrae", substitute --concentrate--. |
| Col. 19, line 44 | Delete "cleracea", substitute --oleracea--. |
| Col. 21, line 50 | Delete "noen", substitute --none--. |
| Col. 24, line 63 | Delete "livetest", substitute --live test--. |
| Col. 26, line 32 | Delete "till", substitute --still--. |
| Col. 26, Table 11, sub-col. 2, title | Delete "compond", substitute --compound--. |
| Col. 27, line 14 | Delete "filld", substitute --filled--. |
| Col. 28, line 11 | Delete "alkoxyalky", substitute --alkoxyalkyl--. |
| Col. 29, line 15 | Delete "$CO_3H_7$", substitute --$SC_3H_7$--. |
| Col. 30, line 35 | Delete "compoun", substitute --compound--. |

UNITED STATES PATENT AND TRADEMARK OFFICE
CERTIFICATE OF CORRECTION

PATENT NO. : 4,112,080
DATED : September 5, 1978
INVENTOR(S) : Hofer et al

It is certified that error appears in the above-identified patent and that said Letters Patent are hereby corrected as shown below:

Col. 30, line 50      Insert -- - -- after "6", before "ox-".

*Signed and Sealed this*

*Twenty-first* Day of *August 1979*

[SEAL]

Attest:

Attesting Officer

LUTRELLE F. PARKER
*Acting Commissioner of Patents and Trademarks*